United States Patent [19]

Gross

[11] Patent Number: 4,473,508

[45] Date of Patent: Sep. 25, 1984

[54] PROCESS FOR THE PRODUCTION OF γ-CHLOROACETOACETIC ACID CHLORIDE

[75] Inventor: Max Gross, Biberist, Switzerland

[73] Assignee: Lonza Ltd., Gampel/Valais, Switzerland

[21] Appl. No.: 493,504

[22] Filed: May 11, 1983

Related U.S. Application Data

[63] Continuation-in-part of Ser. No. 321,042, Nov. 13, 1982, abandoned, which is a continuation-in-part of Ser. No. 197,688, Oct. 16, 1980, abandoned.

[51] Int. Cl.$^3$ ............................................. C07C 51/58
[52] U.S. Cl. ................................. 260/544 Y; 560/145; 560/174; 564/143
[58] Field of Search .................... 260/544 Y; 560/174, 560/145; 564/143

[56] References Cited

U.S. PATENT DOCUMENTS

| | | | |
|---|---|---|---|
| 3,701,803 | 10/1972 | Boosen | 562/577 |
| 3,960,941 | 6/1976 | Wiegand | 260/534 |
| 4,143,067 | 3/1979 | Greth | 260/544 |

FOREIGN PATENT DOCUMENTS

| | | | |
|---|---|---|---|
| 113824 | 10/1976 | Japan | 260/544 |
| 1209725 | 10/1970 | United Kingdom | 562/577 |

OTHER PUBLICATIONS

Perry, Chemical Engineers Handbook, pp. 4–17 to 4–26, McGraw Hill (1968).

Hickinbottom, W. J., "Reactions of Organic Compounds", John Wiley & Sons, pp. 120 to 123 and 402 to 407.

Primary Examiner—James H. Reamer
Attorney, Agent, or Firm—Fisher, Christen & Sabol

[57] ABSTRACT

A process for the production of γ-chloroacetoacetic acid chloride by reaction of chlorine and diketene. The process has a throughput which is from 5 to 750 kg of product per liter reaction volume hour, which means the process achieves a large plant scale throughput of reactants. A solution of chlorine dissolved in an inert solvent and a solution of diketene dissolved in an inert solvent are introduced simultaneously in a continuous current into a tube reactor in such a way that the two solvents immediately mix homogeneously and a turbulent flow develops. The turbulent flow in the tube reactor has a Reynolds number of at least 2,500. None of the reactants or components are used in gaseous form in the reaction, and no gaseous phase forms during the reaction. The mole ratio of chlorine to diketene is between 0.9 to 1 and 1.2 to 1. The same inert solvent can be used in both the chlorine solution and the diketene solution. Preferably a chlorinated hydrocarbon is used as the inert solvent. Preferably both the diketene and chlorine are each used in the form of a 1 to 15 percent by weight solution. Preferably a temperature which lies below the boiling point of the solvent is maintained in the reaction tube.

28 Claims, No Drawings

PROCESS FOR THE PRODUCTION OF γ-CHLOROACETOACETIC ACID CHLORIDE

This a continuation-in-part of U.S. application Ser. No. 321,042, filed Nov. 13, 1982, now abandoned which is a continuation-in-part of U.S. application Ser. No. 197,688, filed on Oct. 16, 1980 now abandoned.

BACKGROUND OF THIS INVENTION

1. Field of this Invention

This invention relates to the production of γ-chloroacetoacetic acid chloride from chlorine and diketene.

2. Prior Art

The production of γ-chloroacetoacetic acid chloride from chlorine gas and diketene is known. The reaction takes place exothermally and therefore requires a large amount of cooling. Undesirable α-chloroacetoacetic acid chloride develops, especially when the reaction proceeds too slowly. According to the Japanese Patent Publication No. 113,824 (1976), such disadvantages are supposedly avoided when dissolved diketene is allowed to flow downwardly in a column reaction vessel at the same time diluted chlorine gas is fed into it in a continuous current or countercurrent manner. However, the process merely leads to selectivities of less than 90 percent. In addition, the monetary expenditure for space and production for such column reaction vessels is undesirably high. Also the capacity of such column reaction vessels is very low because of the relatively small exchange surface and the small flow velocities.

BROAD DESCRIPTION OF THIS INVENTION

An object of this invention is to provide a process which avoids the above-mentioned disadvantages and problems while achieving a high or large plant scale throughput of reactants. Another object of this invention is to provide a process which tends to avoid the formation of undesirable by-products. A further object of this invention is to provide a process which has high reactants selectivity, achieves high throughput of reactants and gives a highly quantitative reaction yield. Another object of this invention is to provide a high throughput process which allows the use of a small reactor. Other objects and advantages of this invention are set out herein or are obvious herefrom to one ordinarily skilled in the art.

The objects and advantages of this invention are achieved by the process of this invention.

This invention involves a process for the production of γ-chloroacetoacetic acid chloride by reaction of chloride and diketene. The process has a large scale plant or high throughput. In the process, a solution of chlorine dissolved in an inert solvent and a solution of diketene dissolved in an inert solvent are simultaneously introduced into a tube reactor in a continuous current in such a manner that the two solvents immediately mix homogeneously and a turbulent flow develops. The turbulent flow in the tube reactor has a Reynolds number of at least 2,300. None of the reactants or components are used in gaseous form in the reaction and no gaseous phase forms during the reaction. The process has throughput which is from 5 to 750 kg of product per liter reaction volume·hour. The molar ratio of chlorine to diketene is between 0.9 to 1 and 1.2 to 1. Preferably the same inert solvent is used in both the chlorine solution and the diketene solution. Preferably a chlorinated hydrocarbon is used as the inert solution. Most preferably methylene chloride is used as the inert solvent. Preferably the chlorine is used in the form of a 1 to 15 percent by weight solution. Preferably the diketene is used in the form of a 1 to 15 percent by weight solution. Also preferably a temperature which lies below the boiling point of the inert solvent is maintained in the reaction tube.

In the process of this invention, the diketene supply, as a 1 to 15 weight percent solution, is 200 l to 2,000 l of solution/l reaction volume, which equals 2.66 kg to 26.6 kg of diketene/l reaction volume·hour, for the 1 weight percent solution, and equals 40 kg to 400 kg of diketene/l reaction volume·hour, for the 15 weight percent solution. The chlorine supply, as a 1 to 15 weight percent solution, is 200 l to 2,000 l of solution/l reaction volume, $\triangle$ 2.66 kg to 26.6 kg of chlorine/l reaction volume·hour, for the 15 weight percent solution. Based upon the above, the total throughput as solution (diketene solution and chlorine solution) is 400 l to 4,000 l of solution/l reaction volume·hour. This results in a capacity of 5 kg to 750 kg of product/l reaction volume·hour, respectively, for 400 l/1 weight percent solution and 4,000 l/15 weight percent solution, or in a minimal throughput of 5 kg of product/l reaction volume·hour and a maximal throughput of 750 kg of product/l reaction volume·hour. Preferably, the throughput of the process is at least 100 kg of product/l reaction volume·hour.

The process is carried out by dissolving the diketene in an inert solvent. Preferably the solvent is a chlorinated hydrocarbon, such as, dichloroethane, dichloropropane, 1-chloro-2-fluoroethane, 1,1-dichloroethane, 1,2-dichloroethane, methyl chloroform, 1-chlorobutane, 2-chlorobutane, 1-bromobutane, ethyl bromide, 1-bromo-2-chloroethane, ethyl chloride, 1-bromo-2-fluoroethane, 1-iodobutane, bromochloromethane, dibromomethane, 1,1-dibromomethane, difluoroiodomethane, 1-bromopropane, bromochlorofluoromethane, 2-bromopropane, bromodichloromethane, bromofluoromethane, bromotrichloromethane, dibromodifluoromethane, pentachloromethane, 1,1,1,2-tetrachloroethane, fluoroiodomethane, iodomethane, diiodofluoromethane, 1,1,2,2-tetrachloromethane, 1,1,2-trichloroethane, 1-chloropropane, 1,2-dibromopropane, 1,2,3-trichloropropane, 1,1,1,2-tetrachloropropane, carbon tetrachloride and chloroform. Most preferably the inert solvent is methylene chloride (dichloromethane). Preferably the concentration of diketene is 1 to 15 percent by weight in the solvent.

Preferably the chlorine is dissolved in an inert solvent to a concentration of 1 to 15 percent by weight. The inert solvent used to dissolve the chlorine is preferably a chlorinated hydrocarbon and is most preferably methylene chloride. Also, preferably the same solvent is used to (separately) dissolve the chlorine and the diketene.

The two dissolved components are simultaneously inserted in a continuous and cocurrent manner into a reaction tube. The reaction starts spontaneously. At the same time, a gas phase is not necessary nor does such a gas phase develop during the process. As compared to known processes, the required reaction space can be kept small since gas does not form and no gas is needed. Also, as a result, expensive processing of exhaust gas is avoided. The reaction tube is dimensioned, corresponding to the quantity (rate) of the product that is to be produced, in such a manner that a turbulent flow develops in the reaction tube as a result of the (partial)

streams of the educts. The turbulent flow achieved in the process of this invention is defined by a Reynolds number which is higher than 2,300, usually higher than 2,500 and preferably between 5,000 and 20,000. Within the scope of this invention a bundle of tube reactors can be used, provided that they are also dimensioned so that formation of a turbulent flow is achieved.

The Reynolds number as such does not exist and cannot be directly measured; the reason for this is that the Reynolds number is a calculated figure obtained from the throughput of the reaction tube. The formula for the Reynolds number is:

$$Re = \frac{2 \cdot R \cdot \bar{v} \cdot e}{\eta}$$

wherein:
  $R$ = radius of the tube
  $\bar{v}$ = average velocity
  $e$ = density
  $\eta$ = kinematic viscosity With a given tube and a known density and viscosity of the reaction mixture, by the choice of the average velocity one can adjust the Reynolds number. Depending on the quantity of the reaction components fed into the reaction tube one can select the velocity. Current preferred practice, as regards the invention process, involves the use of a reaction tube in the form of a Y - the different reaction components are fed into the two arms and directed to the single leg. The means for making the necessary measurements and the calculations based thereon to obtain the Reynolds numbers are well-known to those ordinarily skilled in the art. The invention process requires a Reynolds number of at least 2,300 and usually at least 2,500 throughout the entire tube reactor. An unexpected advantage of this invention is that it allows the use of a short, narrow tube reactor (e.g., 1 meter long and 2 mm wide). The use of such tube reactor allows the achievement and maintenance of such a degree of turbulence throughout the entire tube reactor. Hence, as far as this invention is concerned, the Reynolds number can be measured in place in the tube reactor or throughout all of the tube reactor.

The reaction tube is cooled from the outside preferably by means of brine cooling. The cooling is dimensioned such that the reaction temperature is maintained below the boiling point of the solvent.

The dissolved educts for their part are introduced into the reactor at ambient temperature. In view of the cooling capacity of the apparatus, operation can also be done with precooled educts, for example, as low as $-30°$ C.

The reaction which takes place in the reaction tube is almost quantitative - as a result, in relation to the reaction volume, high throughputs are achieved. In the process of this invention selectivities of over 98 percent are achieved. It is obvious that as a result of such high selectivities, there is only trace formation of undesirable by-products, such as $\alpha$, $\gamma$-dichloroacetoacetic acid chloride.

The longer the reaction time is, the more di- and tri-halogen components that will be formed. This may be explained by the fact that the probability of a halogen atom encountering a molohalogenated molecule becomes greater with increased time. Likewise, for a halogen atom encountering an already di-halogenated molecule - this provides the formation of the tri-halogenated molecule. If the process was executed in a still larger reactor and if the reaction probability is increased of more of the di- and tri- halogenated by-products being formed.

The $\gamma$-chloroacetoacetic acid chloride is separated by distillative separation, especially from the solvent in the reaction mixture. But the $\gamma$-chloroacetoacetic acid chloride can be left in the inert solvent and then reacted in the form of a reaction mixture, for example, by allowing an alcohol, phenol, amine or aniline to flow therein to form the corresponding ester, amide or anilide. By distillative separation of the solvent, the compounds are obtained in a pure form. The distilled solvent freed of accompanying substances can be fed back to the reaction process for use again therein.

By way of summary, $\gamma$-chloroacetoacetic acid chloride is produced from chlorine and diketene. The process has a throughput which is from 5 to 750 kg of product per liter reaction volume·hour, which means the process achieves a large plant scale throughput of reactants. The two starting products are separately dissolved in an inert solvent and are continuously conducted into a tube reactor in a continuous cocurrent manner. The two starting components must immediately be homogeneously mixed and turbulent flow must immediately occur in the tube reactor. When a small reactor volume is used, high yield and selectivity of $\gamma$-chloroacetoacetic acid chloride results. The products can be reacted in a known manner into $\gamma$-chloroacetoacetic acid ester.

DETAILED DESCRIPTION OF THIS INVENTION

As used herein, all percentages, proportions and ratios are on a weight basis unless otherwise stated herein or otherwise obvious herefrom to one ordinarily skilled in the art.

EXAMPLE 1

A reaction tube, having a 1 m length and a hydraulic-inside diameter of 2 mm, was mounted horizontally. While the tube was cooled from the outside with brine of $-20°$ C., the two reactants (in solution form) were fed to the reaction tube in a continuous cocurrent manner. The requisite turbulent flow was achieved and maintained in the reaction tube. The diketene solution consisted of 8.4 kg of diketene (100 moles) and 150 liters of methylene chloride; and the chlorine solution consisted of 7.6 kg of chlorine (107 moles) and 150 liters of methylene chloride. The two solutions were dosed into the tube such that a flow velocity of 1 m/s developed in the tube. The throughput was 162 l of solution/hr. (Throughput resp. reaction volume: 3,600 l of solution/l·hr.) The highest temperature measured in the reaction medium was 21° C. Upon emergence from the reactor, the reaction solution had a temperature of 2° C. The solution emerging to the reactor was taken and cooled to $-15°$ C. The $\gamma$-chloroacetoacetic acid chloride product was reacted with an equimolar quantity of ethyl alcohol to form $\gamma$-chloroacetoacetic acid ethyl ester. Following such, the excess chlorine, as well as the methylene chloride, was removed by distilling it off. Gas chromatographic analysis of the crude $\gamma$-chloroacetoacetic acid ethyl ester showed a content of 98.1 percent thereof (plus 0.4 percent of acetoacetic acid ester, zero percent of $\alpha$-chloroacetoacetic acid ester and 0.3 percent of α, γ-dichloroacetoacetic acid ester).

EXAMPLE 2

Example 1 was repeated, however, 4.2 kg of diketene per liters of methylene chloride and 3.8 kg of chlorine per 150 liters of methylene chloride were used. A flow velocity of 1.66 m/s occurred in the tube reactor. The throughput was 269 l of solution/hr. (Throughput resp. reaction volume : 1,800 l of solution/1·hr.) Analysis of the crude γ-chloroacetoacetic acid ethyl ester showed a content of 96.8 percent thereof.

EXAMPLE 3

Example 1 was repeated, however, 16.8 kg of diketene per 150 liters of methylene chloride and 15.2 kg of chlorine per 150 liters of methylene chloride were used. A flow velocity of 0.5 m/s occurred in the tube reactor. The throughput was 81 l of solution/hr. (Throughput resp. reaction volume : 540 l of solution/1.hr.) The content of the crude γ-chloroacetoacetic acid ethyl ester was 89.1 percent.

EXAMPLE 4

A tube, having a 3 m length and a hydraulic-inside diameter of 4 mm. was used as the reactor. The tube was mounted vertically and was cooled with brine of −10° C. The solutions were fed, in a continuous cocurrent manner, into the head of the reactor. The solutions had the same concentrations as those in Example 3. The flow velocity however was 0.75 m/s. The highest temperature occurring in the reaction medium was 45° C. The throughput was 135 l of solution per hour. (Throughput resp. reaction volume : 900 l of solution/1.hr.) Analysis of the γ-chloroacetoacetic acid ethyl ester showed a content of 92.8 percent.

EXAMPLE 5

Example 4 was repeated, however, 84 kg of diketene per 1,500 liters of methylene chloride and 76 kg of chlorine per 1,500 liters of methylene chloride were used. The flow velocity was 1 m/s. The throughput was 180 l of solution/hr. (Throughput resp. reaction volume: 1,200 l of solution/1.hr.) The content of the crude γ-chloroacetoacetic acid ethyl ester (i.e., ester in the crude mixture) was 95.3 percent.

EXAMPLE 6

U.S. Pat. No. 3,701,803 and British Pat. No. 1,209,725 both deal with a process for halogenating diketene, such process herein being termed the "Boosen laboratory process" or "Boosen process". The following is a comparison of the Boosen laboratory process scaled up and applied as a plant process with the tube-reactor process (i.e., the process of this invention).

Reasons against the transfer of the Boosen process into plant scale are:

| capacity (kg product/time × reaction volume) | |
|---|---|
| tube reactor | 250 kg/l hr. |
| Boosen laboratory process 1 1/1 hr. | 0.15 kg/l hr. |
| Boosen plant process 500 ½ hr. hypothetical | 0.02 kg/l hr. |
| Boosen process 10,000 l/24 to 48 hr. | 25 to 50 kg/l hr. (actually rather less) |

The above table therein compares capacity, with the hypothetical Boosen plant process being a quantum magnitude behind the capacity of the invention's tube reactor. When one scales up from 1 l to 500 l to 1,000 l, the ratio of cooling surface to reaction volume gets smaller and smaller (see below) which results in longer cooling periods and longer periods for chlorine addition in order to enable maintenance of a temperature of less than −10° C. in the agitator.

A temperature increase above −10° C. during a longer period (minutes) causes disintegration of the acid chloride. In the tube reactor, as well, the temperature increased to 30 to 50° C., however, only for less than a second. Then the acid chloride is cooled immediately (2 to 3 sec.) so that no disintegration can occur.

| Ratio of cooling surface to reaction volume | | |
|---|---|---|
| Volume | Cooling Surface | Cooling Surface/ Volume |
| 63 l | 0.63 m² | 10 m²/m³ |
| 630 l | 2.73 m² | 4.3 m²/m³ |
| 6300 l | 14 m² | 2.2 m²/m³ |
| quality (yield of product) | | |
| tube reactor | yield: | 98% |
| Boosen laboratory process, 1 l | yield: | 98% |
| Boosen plant process, 500 l | yield: | <90% |

As one enlarges the agitator, the intermixing of the educts becomes worse.

For the invention's tube reactor, the yield is 98 percent; Boosen's laboratory process, 1 liter reaction the yield is 98 perent; and Boosen's plant process, 500 liter reactor (hypothetical situation), the yield is less than 90 percent. As one enlarges the agitator, the intermixing of the educts becomes worse. In the 500 l agitator it is practically impossible to distribute the chlorine evenly over the entire agitator within less than one second (the reaction time is less than 1 second).

Hence, one ordinarily skilled in the art can readily see why it is virtually impossible to transfer the Boosen reaction process from a 1 liter funnel to a 500 liter reactor. The above also establishes why the process of the invention is unobvious over Boosen to one ordinarily skilled in the art.

EXAMPLE 7

A reactor having interior enameling, a total capacity of 630 liters, an effective capacity of 500 liters and a cooling surface of 2.73 m³, was charged with 500 liters of a 15 weight-percent solution of diketene in methylene chloride, and cooled to −20° C. During a period of about 6 hours, a total of 82 kg of chlorine gas was fed into the reactor. The addition of the chlorine gas was in such a way that the temperature at no time rised above −10° C. The reaction mixture was stirred by means of an impeller during the entire time. To the γ-chloroacetoacetic acid chloride a equimolar quantity of ethyl alcohol was added to form the corresponding γ-chloroacetoacetic ethyl ester. The total reaction time was about two hours. The unreacted excess of chlorine and the methylene chloride were removed by distilling them off. A gas chromatographic analysis showed a yield of:

86 percent of γ-chloroacetoacetic acid ethyl ester
3 percent of acetoacetic acid ester
0 percent of α-chloroacetoacetic ester
8 percent of α, γ-dichloroacetoacetic acid ester and
3 percent of trichloroacetoacetic acid ester.

Due to the long reaction time, it is fully understandable that, beside the undesired α-compound, even undesired dichloro- and even trichloro-compounds are formed.

In addition it can be stated that the yield dropped drastically with increasing volume of the reactor. Thus, when using a 1 liter lab reactor, the yield is about 98 percent, with a 50 liter reactor the yield is about 92 percent with a 500 liter reactor the yield is about 86.4 percent and with a 5,000 liter reactor the yield is probably under 80 percent.

The longer the reaction time is, the more di- and tri-halogen components that will be formed. This may be explained by the fact that the probability of a halogen atom encountering a molohalogenated molecule becomes greater with increased time. Likewise, for a halogen atom encountering an already di-halogenated molecule—this provides the formation of the tri-halogenated molecule. If the process was executed in a still larger reactor and if the reaction time was extended even more, the probability is increased of more of di- and tri- halogenated by-products being formed.

What is claimed is:

1. Process for the production of γ-chloroacetoacetic acid chloride by reacting chlorine and diketene, characterized in that a solution of chlorine dissolved in an inert solvent and a solution of diketene dissolved in an inert solvent are simultaneously introduced in a continuous current manner into a tube reaction in such a way that the two solutions immediately homogeneously mix and a turbulent flow develops in the tube reactor, the mole ratio of chlorine to diketene being between 0.9 to 1 and 1.2 to 1, the throughput for the process is from 5 to 750 kg of γ-chloroacetoacetic acid chloride per liter reaction volume·hour, no reactants or components in gaseous form being used in the reaction, no gaseous phase forming during the reaction and the turbulent flow in the tube reactor has a Reynolds number of at least 2,300.

2. Process as claimed in claim 1 wherein the turbulent flow in the tube reactor has a Reynolds number of at least 2,500.

3. Process as claimed in claim 2 wherein the process throughput is at least 100 kg of γ-chloroacetoacetic acid chloride per liter reaction volume·hour.

4. Process as claimed in claim 2 wherein the same inert solvent is used to separately dissolve the chlorine and the diketene.

5. Process as claimed in claim 4 wherein the inert solvent is a chlorinated hydrocarbon.

6. Process as claimed in claim 4 wherein the chlorine solution contains 1 to 15 percent by weight of chlorine, the diketene solution contains 1 to 15 percent by weight of diketene and the Reynolds number is between 5,000 and 20,000.

7. Process as claimed in claim 6 wherein a temperature, which lies below the boiling point of the solvent, is maintained in the reaction tube.

8. Process as claimed in claim 2 wherein each of the inert solvents is a chlorinated hydrocarbon.

9. Process as claimed in claim 2 wherein a temperature, which lies below the boiling point of the solvent, is maintained in the reaction tube.

10. Process as claimed in claim 2 wherein the Reynolds number is between 5,000 and 20,000.

11. Process as claimed in claim 2 wherein the chlorine solution contains 1 to 15 percent by weight of chlorine and the diketene solution contains 1 to 15 percent by weight of diketene.

12. Process as claimed in claim 2 wherein the same inert solvent is used to separately dissolve the chlorine and the diketene, the chlorine solution contains 1 to 15 percent by weight of chlorine, the diketene solution contains 1 to 15 percent by weight of diketene, and a temperature, which lies below the boiling point of the solvent, is maintained in the reaction tube.

13. Process as claimed in claim 12 wherein the inert solvent is a chlorinated hydrocarbon.

14. Process as claimed in claim 2 wherein the two solutions are simultaneously introduced in a continuous cocurrent manner into the tube reactor.

15. Process as claimed in claim 2 wherein the chlorine solution contains 1 to 15 percent by weight of chlorine, the diketene solution contains 1 to 15 percent by weight of diketene, a temperature, which lies below the boiling point of the solvent, is maintained in the reaction tube, and the Reynolds number is between 5,000 and 20,000.

16. Process as claimed in claim 2 wherein the two solutions are introduced in a continuous cocurrent manner into the tube reactor.

17. Process as claimed in claim 1 wherein the γ-chloro-acetoacetic acid chloride is separated from the reaction mixture by distillative separation.

18. Process for the production of a γ-chloroacetoacetic acid ester, phenolate, amide or anilide comprising (a) reacting chlorine and diketene, a solution of chlorine dissolved in an inert solvent and a solution of diketene dissolved in an inert solvent being simultaneously introduced in a continuous current manner into a tube reaction in such a way that the two solutions immediately homogeneously mix and a turbulent flow develops in the tube reactor, the mole ratio of chlorine to diketene being between 0.9 to 1 and 1.2 to 1, the throughput for the process being from 5 to 750 kg of γ-chloroacetoacetic acid chloride per liter reaction volume·hour, no reactants or components in gaseous form being used in the reaction, no gaseous phase forming during the reaction and the turbulent flow in the tube reactor having a Reynolds number of at least 2,300, whereby γ-chloroacetoacetic acid chloride is formed, and (b) converting the γ-chloroacetoacetic acid chloride into (i) γ-chloroacetoacetic acid ester, (ii) or γ-chloroacetoacetic acid phenolate, or (iii) γ-chloroacetoacetic acid amide, or (iv) γ-chloroacetoacetic acid anilide by reaction with (i) and alcohol or (ii) phenol or (iii) an amine or (iv) aniline, respectively.

19. Process as claimed in claim 18 wherein an inert solvent is present in step (b).

20. Process as claimed in claim 19 wherein the inert solvent is methylene chloride.

21. Process as claimed in claim 19 wherein the inert solvent is a chlorinated hydrocarbon.

22. Process as claimed in claim 18 wherein, in step (b), the γ-chloroacetoacetic acid chloride is reacted with an alcohol, whereby an γ-chloroacetoacetic acid ester is formed.

23. Process as claimed in claim 22 wherein, in step (b), the alcohol is ethanol and the γ-chloroacetoacetic acid chloride is γ-chloroacetoacetic acid ethyl ester.

24. Process as claimed in claim 23 wherein step (b) is conducted at −15° C.

25. Process as claimed in claim 18 wherein, in step (b), the γ-chloroacetoacetic acid chloride is reacted with phenol, whereby γ-chloroacetoacetic acid phenolate is formed.

26. Process as claimed in claim 18 wherein, in step (b), the γ-chloroacetoacetic acid chloride is reacted with an amine, whereby an γ-chloroacetoacetic acid amide is formed.

27. Process as claimed in claim 18 wherein, in step (b), the γ-chloroacetoacetic acid chloride is reacted with aniline, whereby γ-chloroacetoacetic and anilide is formed.

28. Process as claimed in claim 18 wherein the γ-chloroacetoacetic acid ester, phenolate, amide or anilide is separated from the reacted mixture (b) by distillative separation.

* * * * *